United States Patent [19]

Perez

[11] 4,307,044

[45] Dec. 22, 1981

[54] METHOD OF MAKING A CASTING

[76] Inventor: Richard D. Perez, 1114 Mission St., South Pasadena, Calif. 91030

[21] Appl. No.: 163,645

[22] Filed: Jun. 27, 1980

Related U.S. Application Data

[62] Division of Ser. No. 902,885, May 4, 1978, Pat. No. 4,229,170.

[51] Int. Cl.³ ............................................. A61C 13/08
[52] U.S. Cl. ....................................................... 264/19
[58] Field of Search ................. 433/206, 202; 264/19, 264/20; 164/DIG. 4

[56] References Cited

U.S. PATENT DOCUMENTS

| | | | |
|---|---|---|---|
| 448,745 | 3/1891 | Wright | 433/175 |
| 633,071 | 9/1899 | Campbell | 433/206 |
| 2,025,344 | 12/1935 | Fischer | 433/34 |
| 3,052,982 | 9/1962 | Weinstein et al. | 433/206 |
| 3,716,418 | 2/1973 | Kochavi | 433/213 |
| 4,059,901 | 11/1977 | Spalten | 433/192 |
| 4,229,170 | 10/1980 | Perez | 433/206 |

*Primary Examiner*—Gene Mancene
*Assistant Examiner*—John J. Wilson
*Attorney, Agent, or Firm*—Harvey B. Jacobson

[57] ABSTRACT

A pontic having a core constructed from a ceramic material embedded in a metal mass at least a portion of which is itself covered by a layer of porcelain. One or more pins are initially inserted into the core for facilitating placement of the core subsequent to waxing of same into a pattern in the cavity of a mold while the pattern is invested and the metal mass subsequently cast within the investment. The porcelain covering layer can be added to the casting in a conventional manner once the casting has been removed from the mold and cleaned in an appropriate manner.

3 Claims, 6 Drawing Figures

METHOD OF MAKING A CASTING

This is a division of application Ser. No. 902,885, filed May 4, 1978, now U.S. Pat. No. 4,229,170, issued Oct. 21, 1980.

BACKGROUND OF THE INVENTION

1. Field of the Invention

This invention relates generally to dental prosthetic devices, and particularly to a pontic which uses less metal than conventional pontics.

2. Description of the Prior Art

The arrival of porcelain-fused-to-metal, in about 1958, brought a new era to dentistry, and with it, many problems. The patience and skills of dental technicians, with time, were able to solve many of these problems, but the problems that remain are still troublesome.

One of the remaining problems involves casting the framework of the product which is to receive the covering layer of porcelain, and this problem stems from the fact that a replacement tooth is much greater in bulk than the natural teeth which will abut the pontic. This requires that thick, heavy pontics be cast, which often results in porous castings. Further, the conventional castings used in porcelain-fused-to-metal restorations is solid precious or non-precious metal, such as gold, and tends to be rather heavy and highly conductive to heat, causing the patient great discomfort and resulting dissatisfaction with the restoration.

The casting used in porcelain-fused-to-metal pontics in generally made in the conventional manner of constructing pontics by the well-known investment or "lost wax" process. A discussion of the use of this process as it applies to the manufacture of dental prosthetic devices can be found in U.S. Pat. No. 4,024,211, issued May 17, 1977, to A. E. Strauss.

SUMMARY OF THE INVENTION

It is an object of the present invention to provide a porcelain-fused-to-metal pontic which is lighter and denser than pontics constructed by conventional techniques, and which eliminates the problem of the metal in the pontic becoming porous as the molten metal solidifies.

Another object of the present invention is to provide a stronger and lighter substructure for a dental pontic for facilitating fusing of porcelain to the substructure.

Yet another object of the present invention is to provide a procelain-fused-to-metal pontic construction which reduces the amount of metal used, which reduction is particularly advantageous in monetary savings when the metal used is a precious metal.

A still further object of the invention is to provide a pontic which can be constructed in less time than when conventional construction techniques are employed, yet is stronger in construction than strength realized from conventional techniques.

Still another object of the invention is to provide a porcelain-fused-to-metal pontic, the metal of which is easier to polish because of the relatively higher density of the casting used in the pontic.

Yet another object of the present invention is to provide a pontic which is more comfortable to wear because of lighter weight and lower heat conductivity.

These and other objects are achieved according to the present invention by providing a pontic having: a core; a metal mass disposed around and embedding the core; and a covering layer over at least a portion of the metal mass. The core preferably is solid and constructed from a ceramic material, while the covering layer is usually formed of porcelain fused to the metal by techniques known per se.

A pontic according to the invention is first constructed by making a pattern composite of wax and the core, and subsequently investing the pattern and removing the wax therefrom in a conventional manner in a mold, leaving the core and investment material to form a pattern which can be cast in a conventional manner with a precious or non-precious metal. Once cast, the investment material and casting are removed from the mold cavity, with the investment material being separated from the casting in a conventional manner and the surface of the casting cleaned as appropriate. One or more pins which are attached to the core initially in order to permit the core to be affixed within the mold cavity can now be cut off flush with the outer surface of the casting, and porcelain or a similar material applied to at least a portion of the outer surface of the metal mass by techniques known per se.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
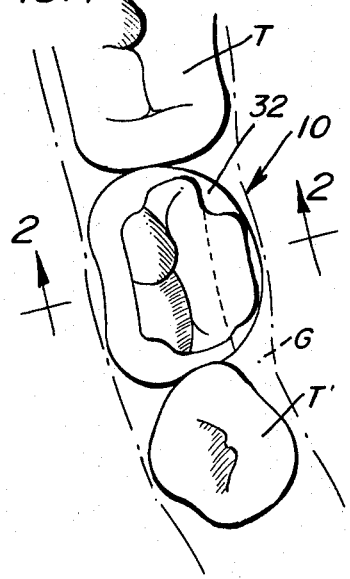
FIG. 1 is a fragmentary, top plan view, showing a pontic according to the present invention in place between two abutment teeth in an edentulous area of a person's mouth.
Figure 2:
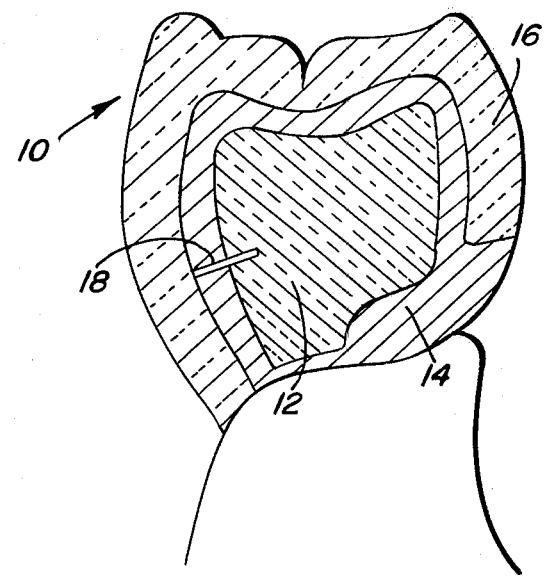
FIG. 2 is an enlarged, fragmentary, sectional view taken generally along the line 2—2 of FIG. 1.
Figure 3:
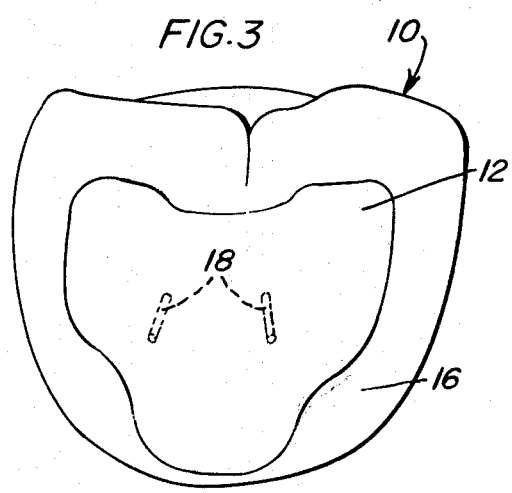
FIG. 3 is a schematic, front elevational view of a pontic constructed in accordance with the present invention.
Figure 4:
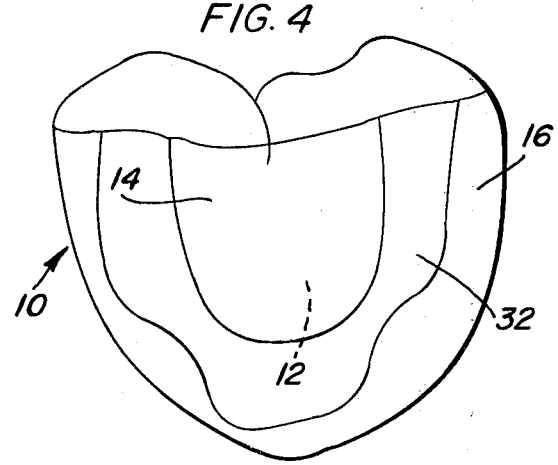
FIG. 4 is a schematic, rear view of the pontic seen in FIG. 3.

Referring now more particularly to FIGS. 1 through 4 of the drawings, a pontic 10 according to the present invention, which is shown in FIG. 1 as being disposed between abutment teeth T and T' in an edentulous area of a person's mouth, comprise a core 12, constructed from a suitable ceramic material, and the like, embedded in a metal mass 14 disposed around core 12, and itself at least partially covered by a covering layer 16 of porcelain, and the like. By "ceramic" is meant the traditional ceramic materials based on silica, which is fused and molded in a conventional manner. Since neither the specific material used in nor the exact manner of fabricating the core 12 of pontic 10 forms part of the present invention, it will not be described in greater detail herein. A pair of pins 18 are illustrated as being embedded in the core 12 and associated metal mass 14 of pontic 10, the purpose of which pins and the manner in which they become embedded in a finished pontic 10 is to be made clear below.

In constructing a pontic 10 according to the invention, a model or pattern is constructed and articulated in the usual manner. More specifically, the abutments are first waxed, then the pontic, by placing two thickness of 26 gauge wax on a stone model (not shown) over the ridge area that is to be bridged with a pontic 10. Then a core 12 of the proper size and shape is selected and aligned. Casting rings 22 are commonly used in dentistry to invest wax patterns. A rubber or metal crucible former 24 disposed at the bottom of ring 22 forms a well in the investment material 26 to guide molten metal to sprues 28 and ultimately to the mold left by removal of the wax pattern during investment. The abutments and pontic are cast as one unit.

After two thickness of 26 gauge wax has been formed to the stone model of the ridge of the lower jaw, then the internal core 12 is placed on the wax in proper alignment by flowing a little soft causing wax to hold the core 12 in place. Once the core 12 is in place, a flow of inlay wax can be placed around core 12 to secure it in such proper position, keeping the wax short of the occusal surface formed by edge 30 of core 12 in case you have to reduce the core. A space for bar 32 is filled in prior to casting before the pattern is adjusted, as by grinding an edge 30 for occusal clearance. The grinding of edge 30 should not introduce chips into the wax so as to cause pits in the castings made from the mold. After the latter mentioned adjustment, residue from the grinding must be rinsed off, as with water, before the wax-up of the pattern on the stone model can be continued.

Figure 5A:
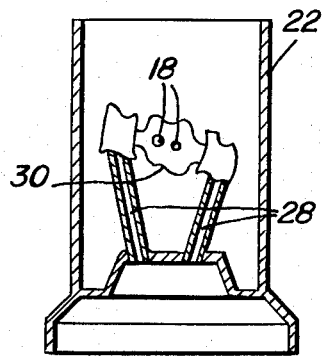
FIGS. 5-A, and 5-B are schematic diagrams showing various steps in the process according to the invention of making a pontic according to the invention.
Figure 5B:
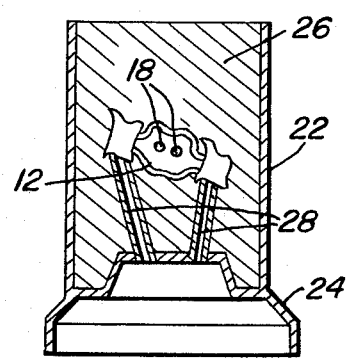

As the pattern is waxed, care must be taken not to wax over the extended portions of pins 18, which as can be seen from FIGS. 5-A and 5-B initially extend a substantial distance from core 12 so as to terminate adjacent ring 22. These pins 18 hold the resulting pattern in an investment material 26 while casting is being done. Once the pattern is in place within ring 22, an investment material 26 is placed in ring 22 in a conventional manner so that the wax is lost and the investment material 26 forms a mold for the casting. Pins 18 are embedded in material 26 so as to hold core 12 in place during casting. The casting operation can now be carried out in a conventional manner and when finished, the resulting casting removed from ring 22, together with material 26, and cleaned, the pins 18 cut off, and the resulting subframe finished to receive the porcelain, and the like. The latter is placed on the stone model so as to form the covering layer 16 and finish off the pontic 10.

Pins 18 extend from the wax pattern approximately ⅜″, for example, to be held in position by the investment material 26 while the molten metal which will form the casting is being introduced into the mold left by wax after the latter has been removed in the conventional manner during the investment.

A minimum of ¾ of a millimeter of wax should be placed around core 12 when forming the pontic, with the result that the metal mass 14 will be at least ¾ of a millimeter thick. When grinding core 12 for occlusal clearance, one should be sure to keep the wax away from the area to be ground. Further, the residue of any wax affected by the grinding should be cleaned completely from the surface of core 12, or from the pattern being made, before the waxing procedure is continued. The ¾ millimeter minimum thickness of metal in metal mass 14 assures that one will not grind through to core 12 during finishing operations of the final casting.

The frame resulting from the casting has the necessary strength for a successful bridge due to additional support stresses resulting from the composite construction. The best size suited for the space to be filled must be selected, and by properly visualizing the need beforehand, unnecessary failures in sizing can be eliminated. In this regard, important areas to note are the buccal, mesial and distal.

As can be appreciated from the above description and from the drawings, a pontic constructed in accordance with the present invention provides a light weight, yet dense and very strong, restoration for placement in an edentulous area of a person's mouth so as to provide the person with an efficient and comfortable pontic. The cores will be made in shapes and sizes to fit inside pontics intended to replace centrals and laterals (incisors), cuspids (canines), bicuspids, and molars. These different cores also will be in three basic sizes, for example, such as large, medium and small.

Further, the ceramic core technique can be used in making jewelry, art objects and be used in other industries that use wax elimination techniques.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. The method of casting of a pontic, comprising the steps of:
    (a) making a pattern composite of wax and a pontic core from ceramic material;
    (b) investing the pattern and removing the wax, leaving the pontic core and investment material to form a mold;
    (c) casting a pontic in the mold to embed the core in a relatively thin metal mass;
    (d) removing the investment material and casting from the mold; and
    (e) covering at least a substantial portion of the metal with an outer layer formed of porcelain fused to the metal mass to provide a pontic of lightweight construction having high strength characteristics with minimum distortion, porosity and heat conduction.

2. A method as defined in claim 1, wherein the step of investing and removing includes the step of placing the pattern of a pontic in a mold ring with an unwaxed pin extending from the core and directed toward one of the labial and buccal portions of the pattern of the pontic being made.

3. A method as defind in claim 2, wherein the steps of removing the investment material and casting from the mold includes the steps of cleaning the casting and of severing the pin at the surface of the casting, both prior to the step of covering the casting with a porcelain.

* * * * *